United States Patent
Spears et al.

(10) Patent No.: US 10,318,001 B1
(45) Date of Patent: Jun. 11, 2019

(54) DYNAMIC INTERFACE FLOW BASED ON DEVICE LOCATION

(71) Applicant: United Services Automobile Association (USAA), San Antonio, TX (US)

(72) Inventors: James Malcolm Spears, San Antonio, TX (US); John David Clark, Boerne, TX (US); Lisa Horgan, San Antonio, TX (US); John David Windham, Fredericksburg, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 15/497,750

(22) Filed: Apr. 26, 2017

(51) Int. Cl.
| | | |
|---|---|---|
| *H04W 4/021* | (2018.01) | |
| *G06F 3/01* | (2006.01) | |
| *H04W 8/18* | (2009.01) | |
| *G01S 5/02* | (2010.01) | |
| *G06F 3/0481* | (2013.01) | |

(52) U.S. Cl.
CPC ............ *G06F 3/015* (2013.01); *G01S 5/0242* (2013.01); *H04W 4/021* (2013.01); *H04W 8/18* (2013.01); *G06F 3/0481* (2013.01)

(58) Field of Classification Search
None
See application file for complete search history.

(56) References Cited

U.S. PATENT DOCUMENTS

| | | | | |
|---|---|---|---|---|
| 2004/0029567 | A1* | 2/2004 | Timmins | H04M 3/4931 455/412.1 |
| 2010/0291907 | A1* | 11/2010 | MacNaughtan | G06Q 30/0241 455/414.1 |
| 2014/0006451 | A1* | 1/2014 | Mullis | G06Q 20/18 707/784 |
| 2016/0165403 | A1* | 6/2016 | Turner | H04W 4/028 455/456.3 |
| 2016/0242010 | A1* | 8/2016 | Parulski | H04W 4/04 |

* cited by examiner

*Primary Examiner* — Mazda Sabouri
*Assistant Examiner* — Xiang Zhang
(74) *Attorney, Agent, or Firm* — Fletcher Yoder, P.C.

(57) ABSTRACT

Techniques are described for dynamically determining the flow of screens to be presented in a user interface (UI) of an application executing on a computing device, based at least partly on a detected presence of a user device (e.g., a portable computing device) in a particular geographic area. Area designation data is transmitted to, and stored on, a user device. The area designation data can describe a geofenced area and/or beacon signals. In response to determining that the user device is in the geographic area indicated by the area designation data, the user device may transmit an alert signal that causes an interface flow to be dynamically determined and executed for an application executing on the computing device that is separate from the user device.

20 Claims, 7 Drawing Sheets

DYNAMIC INTERFACE FLOW BASED ON DEVICE LOCATION

BACKGROUND

Various techniques are currently used to determine the location of a computing device. For example, a network transceiver on a device may be employed to receive signals transmitted through a satellite-based navigation system, such as a version of the Global Positioning System (GPS) or the Global Navigation Satellite System (GLONASS). Based on the signals, the geographic location of the device may be determined to a level a precision that is at least based on the signal characteristics. Device location may also be determined based on other techniques, such as the detection of signals from cellular telephone networks, wireless local area networks based on a version of the IEEE 802.11 standard, or other types of networks. Applications have been developed to leverage device location information, by presenting location-based information to a user. In particular, the location of a computing device, such as a smartphone, may be determined on the device and used by an application to present content on the device, such as map information, route information, information regarding nearby businesses or geographic features, and so forth.

SUMMARY

Implementations of the present disclosure are generally directed to modifying an application flow based on the determined location of a computing device. More specifically, implementations are directed to determining that a computing device is in a particular designated area, based on geofencing, wireless beacon detection, and/or other techniques, and based at least partly on the detected presence of the computing device in a particular area, dynamically determining a flow of an application interface executing on another computing device.

In general, innovative aspects of the subject matter described in this specification can be embodied in methods that includes actions of: providing, by the computing device, area designation data that is transmitted to a portable computing device; receiving, by the computing device, an alert signal that is transmitted from the portable computing device to indicate that the portable computing device is within a geographic area corresponding to the area designation data, as determined on the portable computing device based on the area designation data; accessing user data associated with a user of the portable computing device, the user determined based at least partly on an identifier (ID) communicated by the alert signal; and responsive to receiving the alert signal by the computing device, and based at least partly on the user data, dynamically determining a user interface (UI) flow of an application that is executing on the computing device.

Implementations can optionally include one or more of the following features: the ID is a device ID that identifies the portable computing device; the user is determined based on an association of the device ID with the user in a data structure accessible from the computing device; the ID is a user ID that identifies the user; the actions further include launching, on the computing device, the application with the dynamically determined UI flow, responsive to receiving the alert signal and based at least partly on the user data; the area designation data indicates the geographic area with reference to one or more geographic coordinates; the determination that the portable computing device is within the geographic area is based on a comparison of the area designation data to a current location of the portable computing device; the area designation data indicates the geographic area as one or more polygons each demarcated based on a respective set of geographic coordinates; the area designation data indicates the geographic area with reference to at least one beacon signal; the determination that the portable computing device is within the geographic area is based on detecting the at least one beacon signal at the portable computing device; at least a portion of the user data is presented within the application; the actions further include determining a state of the user of the portable computing device based at least partly on biometric data describing at least one physiological characteristic of the user; the actions further include indicating the state of the user in the application; and/or the UI flow of the application is further determined based on the state of the user.

Other implementations of any of the above aspects include corresponding systems, apparatus, and computer programs that are configured to perform the actions of the methods, encoded on computer storage devices. The present disclosure also provides a computer-readable storage medium coupled to one or more processors and having instructions stored thereon which, when executed by the one or more processors, cause the one or more processors to perform operations in accordance with implementations of the methods provided herein. The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Implementations of the present disclosure provide one or more of the following technical advantages and/or improvements over previously available solutions. Implementations provide for the dynamic determination of a user interface (UI) flow of a service representative (SR) application, as a just-in-time contextual flow. Implementations also provide for a dynamic determination of a particular portion of the user data to present in the UI of the SR application. Such dynamic adjustment of the presentation of information in the UI enables implementations to provide a rule-based, user-customized, concierge-type service from SR to user when the user is in the vicinity of the SR (e.g., in the area of service). This dynamic adjustment of presented data provides a technical improvement and/or advantage over existing systems that may populate a UI based on static data, in the same manner in any given situation, and that are not capable of dynamically adjusting the flow of the UI in response to particular circumstances. Moreover, by dynamically pre-populating a UI with user data that is relevant to a particular situation, and by dynamically adjusting the UI flow for a particular situation, implementations present information in a SR application more efficiently than traditional systems that present the same information in the same manner in each instance. Accordingly, traditional systems may require additional user input, additional processing, additional data storage accesses, and/or additional network communications to get the SR application into a state where it can be used to adequately provide service to a user. By avoiding such additional preliminary operations, implementations make more efficient use of processing power, network capacity, storage capacity, active memory, and/or other computing resources compared to traditional systems.

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Figure 1A:
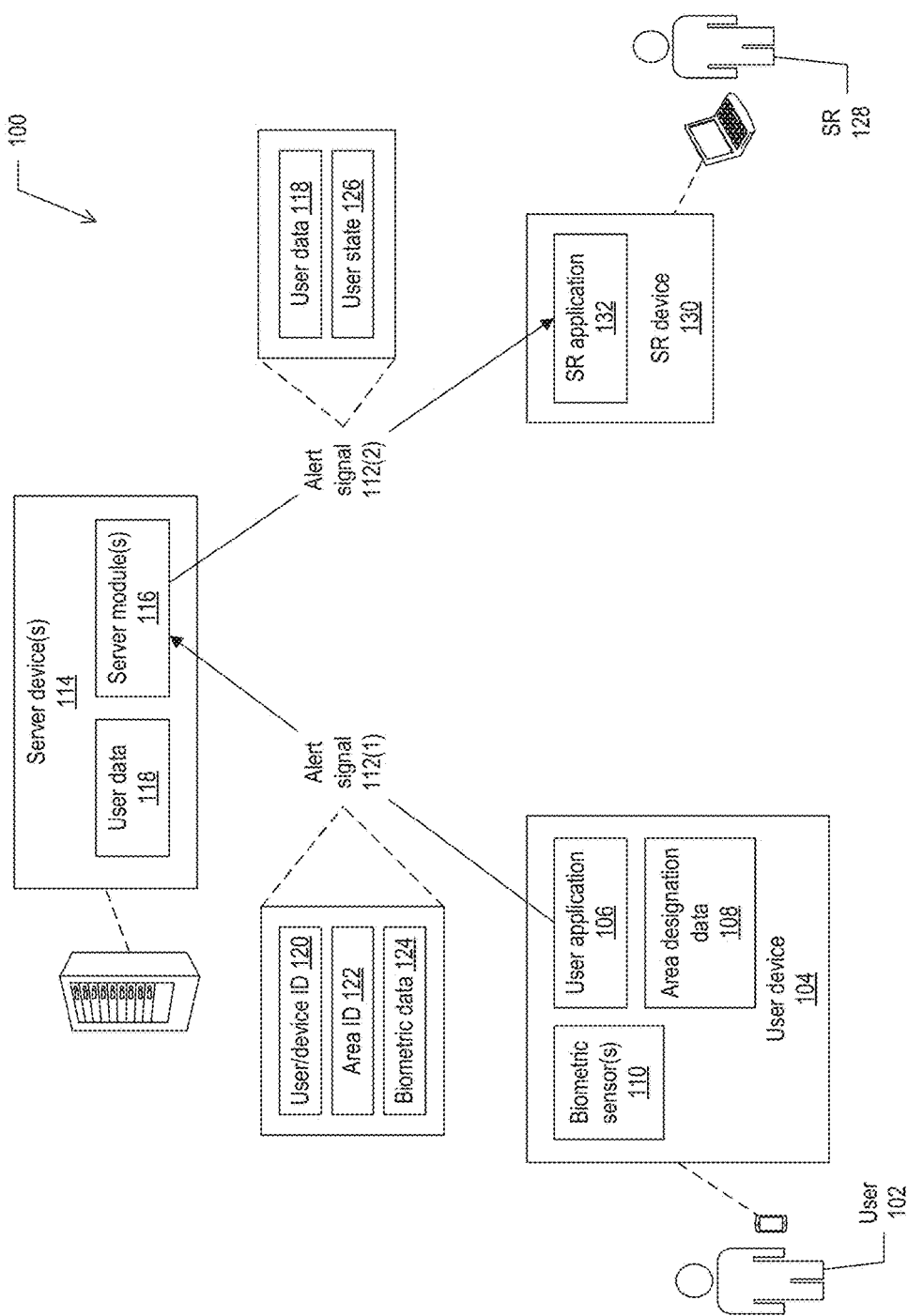
FIG. 1A depicts an example system for determining an interface flow for an application, according to implementations of the present disclosure.

Implementations of the present disclosure are directed to systems, devices, methods, and computer-readable media for dynamically determining the flow of screens to be presented in a user interface (UI) of an application executing on a service representative (SR) computing device, based at least partly on a detected presence of another computing device, a user device, in a particular geographic area. In some implementations, area designation data is transmitted to, and stored on, a user device. The user device may be a portable computing device such as a smartphone, tablet computing device, wearable computer, and so forth. An application executing on the user device may use the area designation data to determine whether the user device is currently in a geographic area indicated by the area designation data. In some implementations, the area designation data may describe a geofenced area, with boundaries described by pairs of geographic coordinates (e.g., in longitude and latitude). The application on the user device may determine whether the user device is currently in the geographic area by comparing a current location of the user device (e.g., determined through GPS or other methods) to the to the geofenced area bounded as described in the area designation data. In some implementations, the area designation data may describe characteristics of one or more beacon signals, such as the frequency of the beacon signal(s) and/or a particular identifier that is broadcast in the beacon signal(s). The application on the user device may determine that the user device is currently in the geographic area based on a detection of the beacon signal(s) at the user device (e.g., received through a wireless transceiver of the user device).

In response to determining that the user device is in the geographic area indicated by the area designation data, the application may instruct a transceiver of the user device to transmit an alert signal indicating the presence of the user device in the area. The alert signal may include an area identifier (ID) to identify the particular area that the user device has entered. The alert signal may also include an ID of the user device and/or the user of the user device that has entered the area. In response to the alert signal, an interface flow may be dynamically determined for a service representative (SR) application that executes on a SR computing device, a separate device from the user device. A flow describes a particular order of screens (also described as pages) to be presented in a user interface (UI) of the SR application. A flow may also describe a timing of the screens to be presented, such as how long each of the screens is presented before moving on to present the next screen.

A flow may be dynamically determined based on the particular area that has been entered, and based on the particular user of the user device that has entered the area. A dynamic determination describes a determination that is made on-the-fly (e.g., in real time) with respect to receiving the alert signal indicating the presence of the user's user device in the area. A dynamic determination of the flow may be made such that the presented flow is not static and is not predetermined prior to receiving the alert signal. For example, a first user entering the area may trigger a flow in which screen A is presented initially in the UI of the SR application, followed by screen B, whereas a second user entering the area may trigger a flow in which screen B is presented initially, followed by screen C, followed by screen A. A different flow may be a different order of presented screens, a presentation of different screens, and/or a different time duration for presenting screens.

The flow determination may be made in real time with respect to receiving the alert signal. A real time operation describes an operation which is performed within a short period of time of a triggering event. A real time operation is performed without unnecessary delay following the triggering event, apart from the delay that is involved in communicating data over networks and/or system buses, performing database operations, performing the requisite operations by processing units, and other types of (e.g., unavoidable) delay. A real time operation may be an operation that is performed in the same execution path, thread, and/or process as the operation that detects the triggering event. In some instances, a real time operation may be an operation that is caused by a message and/or communication that is sent in response to detecting the triggering event. A real time operation may synchronous with respect to detecting the triggering event. A real time operation may be described as dynamic with respect to the triggering event. In some implementations, the determination and/or presentation of the particular UI flow in the SR application may be performed dynamically with respect to a triggering event that is the receipt of the alert signal indicating the presence of the user (and/or the user's user device) in the geographic area.

In some examples, a geofence may be designated to demarcate an area of service around a particular location, such as the location of a bus or other vehicle parked in the vicinity of a natural disaster or other catastrophic event. Alternatively, a transmitter may be set up near the vehicle to transmit a beacon signal to define the area of service. The vehicle may support one or more SRs who are on-site to provide assistance to users who have suffered property damage caused by the event. For example, the SRs may be insurance representatives on-site to assist users with insurance claims, reimbursements, temporary housing stipends, and/or other issues. When a user enters the area of service, carrying their user device for example, the alert signal may be sent from the user device to indicate the user's presence in the area of service. The SR device(s) of the SR(s) may then dynamically determine and present a UI flow according to the user's particular needs. For example, if it is determined that the user needs to complete a claim form, the UI flow may prioritize the particular screen to facilitate completing the form. The form may be pre-populated with user data for the particular user, such as the user's name, policy number, address information, other contact information, coverage information, family members, and so forth. Thus, when the user enters the area of service (e.g., breaks the geofence), the SR application may automatically display information regarding the user, and the SR(s) may be alerted to the particular needs and/or situation of the user, and begin interacting with the user in a proactive manner to resolve their issues more quickly.

In some examples, a geofence and/or beacon signal may be designated to indicate a service area that is a facility for vehicle maintenance and/or repair (e.g., a repair shop). The system may detect when a user enters the area of service, and a SR application may be pre-populated with information regarding that particular user, such as the insurance information for the user, the vehicle they drive, repair history, and so forth. The UI flow of the SR application may be dynamically determined to prioritize a page for a repair appraisal and/or information claim, and the page may be pre-populated with (e.g., header) information to initiate the appraisal and/or claim process. Such automatic identification of the user and dynamic UI flow determination may save the user the time and effort of identifying themselves and explaining their situation. In some instances, the system may have received telematics information from the user's vehicle indicating that an accident has occurred. In such instances, the user data for the particular user may describe the accident, and such data may also be used to pre-populate the UI of the SR application.

In some examples, a geofence and/or beacon signal may be designated to indicate a service area that is a business such as a store (e.g., a vehicle dealership). The system may detect when a user enters the area of service, and the SR application may be pre-populated with information regarding that particular user, such as their recent purchases, interests, tastes in possible products to be purchased, and so forth. As another example, a geofence and/or beacon signal may be designated to indicate a service area that is a hospital, such that the SR application is pre-populated with information regarding the user (e.g., a patient) in response to the alert signal indicating the user's presence in the area. In these and other examples, the UI flow of the SR application may be dynamically determined to optimally service the user, given their particular needs and/or situation.

In some implementations, information may also be transmitted to and presented on the user device in response to detecting the user's presence in the area of service. For example, when entering a vehicle dealership, a user application on the user device may present information regarding vehicles that are on-site that the user may be interested in (e.g., based on the user's previously indicated preferences and/or searches for vehicles). The user application may also present, to the user, relevant information regarding financing for the vehicle, insurance for the vehicle, total cost of ownership, and so forth.

Figure 1B:
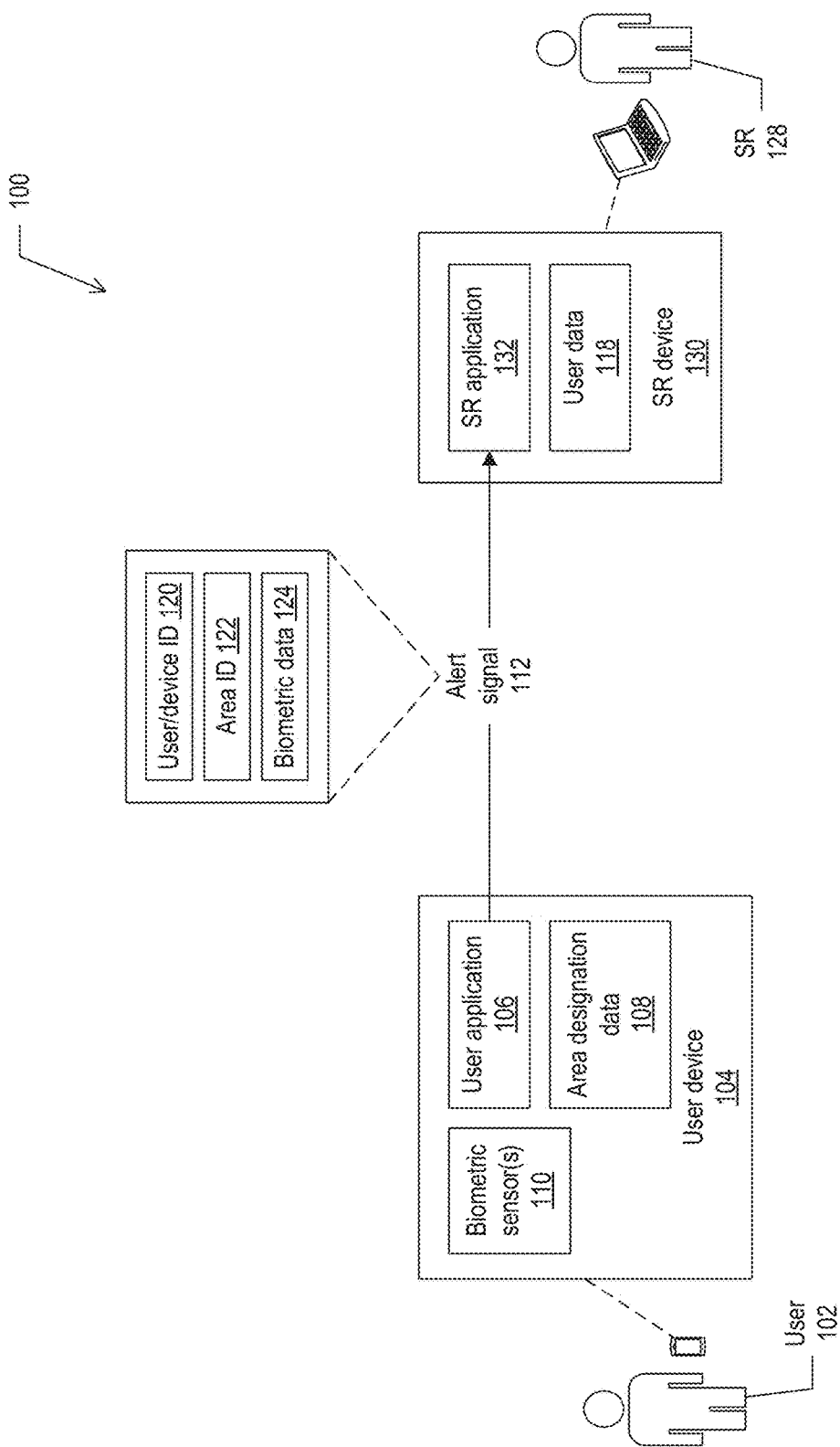
FIG. 1B depicts an example system for determining an interface flow for an application, according to implementations of the present disclosure.

FIGS. 1A and 1B depict two examples of a system 100 for determining an interface flow for a SR application, according to implementations of the present disclosure. In the example of FIG. 1A, a user device 104 is operated by a user 102. In some implementations, the user device 104 is a portable computing device, such as a smartphone, wearable computer, tablet computer, and so forth. The user device 104 may also be any other suitable type of computing device. The user device 104 may execute a user application 106, which accesses area designation data 108 stored on the user device 104 or elsewhere.

In some instances, the area designation data 108 may have been downloaded to the user device 104, and stored on the user device 104 or elsewhere, prior to the user 102 entering the area of service with the user device 104. The user application 106 may employ the area designation data 108 to determine whether the user device 104 is currently within the area of service indicated by the area designation data 108.

In some implementations, the area designation data 108 describes a geofenced area of service. The area may be defined as a set of one or more polygons, the boundaries of each polygon specified as a set of multiple points described by coordinates (e.g., latitude and longitude). For example, a rectangular area may be defined as a set of four points, with each point described as latitude and longitude coordinates. As another example, an area may be defined as two or more contiguous rectangles (or other types of polygons), each described as a set of four points (or N points for an N-sided polygon). In some instances, the area may be defined as a particular location and a radial distance from the location, such that the area is circular. In some instances, the area may be defined as multiple circular areas, each designated with a location and a radius. The user application 106 may periodically compare the current location of the user device 104 (e.g., determined through GPS signals or other methods) to the area designation data 108 to determine whether the user device 104 is current in the designated area.

In some implementations, the area designation data 108 describes one or more beacon signals that are transmitted to define an area of service. The area designation data 108 may describe, for each of the beacon signals, a set of characteristics of the beacon signal. Such characteristics may include a frequency of the beacon signal and/or a particular identifier or other information being broadcast over the beacon signal. The user application 106 may periodically check whether the user device 104 in in range of the one or more beacon signals, such that a wireless transceiver of the user device 104 has received at least one of the beacon signals. In such examples, the detection of a beacon signal may be used by the user application 106 to infer that the user device 104 is in the area of service.

On determining that the user device 104 is in the area of service indicated by the area designation data 108, the user application 106 may instruct a transceiver of the user device 104 to transmit an alert signal 112(1) to indicate the presence of the user device 104 and/or the user 102 in the area of service. In some implementations, the alert signal 112(1) may include an area ID 122 that identifies the particular area that the user device 104 is in. The alert signal 112(1) may also include an ID that identifies the user 102 and/or the user device 104.

In the example of FIG. 1A, the alert signal 112(1) is sent from the user device 104 to server module(s) 116 executing on one or more server devices 114. The server device(s) 114 may include any suitable number and type of computing device. The server module(s) 116 may retrieve user data 118 that is associated with the user ID and/or device ID 120 conveyed in the alert signal 112(1). In implementations where the alert signal 112(1) includes a user ID 120, such as an ID (e.g., username) of the user 102 who is currently logged into the user application 106, the user data 118 for the user 102 may be retrieved from data storage using the user ID as a key. In implementations where the alert signal 112(1) includes a device ID 120, the user data 118 for the user 102 may be retrieved from data storage using the device ID as a key. Alternatively, a lookup table may associate the device ID with a particular user ID (e.g., indicating the user 102 as a registered owner or operator of the particular user device 104). In such instances, the lookup table may be employed to determine the user ID associated with the device ID, and the user ID may then be used to retrieve the user data 118 for the user 102.

The server module(s) 116 may transmit a modified version of the alert signal 112(2) to a SR application 132 executing on a SR device 130 of a SR 128. The SR device 130 may be any suitable type of computing device. In some implementations, the alert signal 112(2) may be sent to one or more SR devices 130 that are particularly determined based on the area ID 122. For example, the alert signal 112(2) may be sent to SR device(s) 130 that are on-site (e.g., physically located) in an area of service identified by the area ID 122 that the user 102 has entered. The alert signal 112(2) may include the particular user data 118 that is associated with the user 102, retrieved based on the user ID and/or device ID 120.

In response to receiving the alert signal 112(2), the SR application 132 may dynamically determine and/or present its UI flow based on the particular user data 118. As described above, the flow may be determined such that it is tailored according to the particular characteristics of the user 102 who has entered the area of service.

In some implementations, the user device 104 may include (and/or be in communication with) one or more biometric sensors 110 that collect biometric data 124 describing physiological characteristics of the user 102. For example, the biometric sensors 110 may collect biometric data 124 describing the user's heart rate, pulse, perspiration level, blood sugar level, neural activity (e.g., brain wave activity), and/or other information. The biometric data 124 may be collected when the user 102 enters the area of service, as determined by the user application 106. In some instances, the biometric data 124 is collected through ongoing monitoring of the user's physiological characteristics, and a current set of biometric data 124 may be retrieved by the user application 106 when the user 102 enters the area of service. The biometric sensor(s) 110 may be incorporated into the user device 104, and/or may be external to the user device 104 and in communication with the user device 104. For example, the user's smartphone may receive biometric data 124 collected by a fitness monitoring wearable computing device that is wirelessly connected to the smartphone.

At least a portion of the biometric data 124 may be included in the alert signal 112(1) sent to the server module(s) 116. The server module(s) 116 may analyze the biometric data 124 to determine a current user state 126 of the user 102 when the user enters the area of service. For example, the biometric data 124 may be employed to determine whether the user 102 is calm, angry, agitated, anxious, panicked, and/or in some other state. The determined user state 126 may be sent to the SR application 132 in the alert signal 112(2), and may be presented in the SR application 132. In some instances, the UI flow of the SR application 132 may be further based on the user state 126. For example, a particular screen may be shown initially if the user 102 is in a calm state, and a different screen may be shown initially if the user 102 is in an agitated state.

In the example of FIG. 1B, the alert signal 112 is sent from the user device 104 to the SR device(s) 130, based on the determination that the user device 104 is in the area of service, without passing through server device(s) as an intermediary. In such examples, the alert signal 112 may include the user ID and/or device ID 120, the area ID 122, and/or the biometric data 124 as described above. In some implementations, the alert signal 112 may be sent over a short-range, radio-frequency communication protocol, such as a version of a near field communication (NFC) protocol, Bluetooth™, or Bluetooth Low Energy (BLE)™. The alert signal 112 may also be sent over other types of networks, such as a local area network (LAN), wide area network (WAN), the internet, and so forth. Based on the user ID and/or device ID in the alert signal 112, the SR application 132 may retrieve user data 118 corresponding to the particular user 102, as described above. The user data 118 may be stored on the SR device 130 and/or elsewhere.

The SR application 132, in either of the examples of FIGS. 1A and 1B, may employ a set of rules to determine the UI flow of the SR application 132 and/or what user data 118 to present within the UI of the SR application 132, based on receiving the alert signal and/or based on the particular user 102 who has entered the area of service. The rules may indicate a different flow and/or different set of presented user data for different circumstances.

Although examples herein describe the user device 104 as a portable computing device, such as a smartphone, implementations are not limited in this way. In some implementations, the user 102 may be carrying an object that includes a radio frequency identification (RFID) tag or other device that is configured to emit a signal. The user's presence in the area of service may be determined based on detecting the signal emitted from the device. Alternatively, the user's presence in the area of service may be determined based on facial recognition, gait recognition, a scanned fingerprint of the user, and/or other types of biometric data that are used to identify the user 102. The user's presence in the area of service may also be determined based on recognizing the user's vehicle license tag number.

In some implementations, machine learning and/or artificial intelligence may also be used to determine the user data to present in the SR application 132 and/or to determine the UI flow of the SR application 132. For example, the SR application 132 may be placed into an initial state, with regard to the user data shown in the UI and the particular flow of the UI, based on the user data 118 and the presence of the user 102 in a particular area of service. The initial state may be determined based on a model that determines the state based on a set of rules, to present particular data in a particular order according to the user and/or the situation (e.g., the particular location and/or nature of the area of service established to service the user). That state may be monitored to determine how the SR 128 modifies the state, by changing the UI flow and/or requesting different user data to be used to populate the UI. Based on the monitored modifications, a model may be refined and/or retrained. Across multiple iterations of servicing a particular user or population of users, the model may be improved to provide a more efficient initial state of the SR application based on detecting the presence of a user in the area of service.

Figure 2:
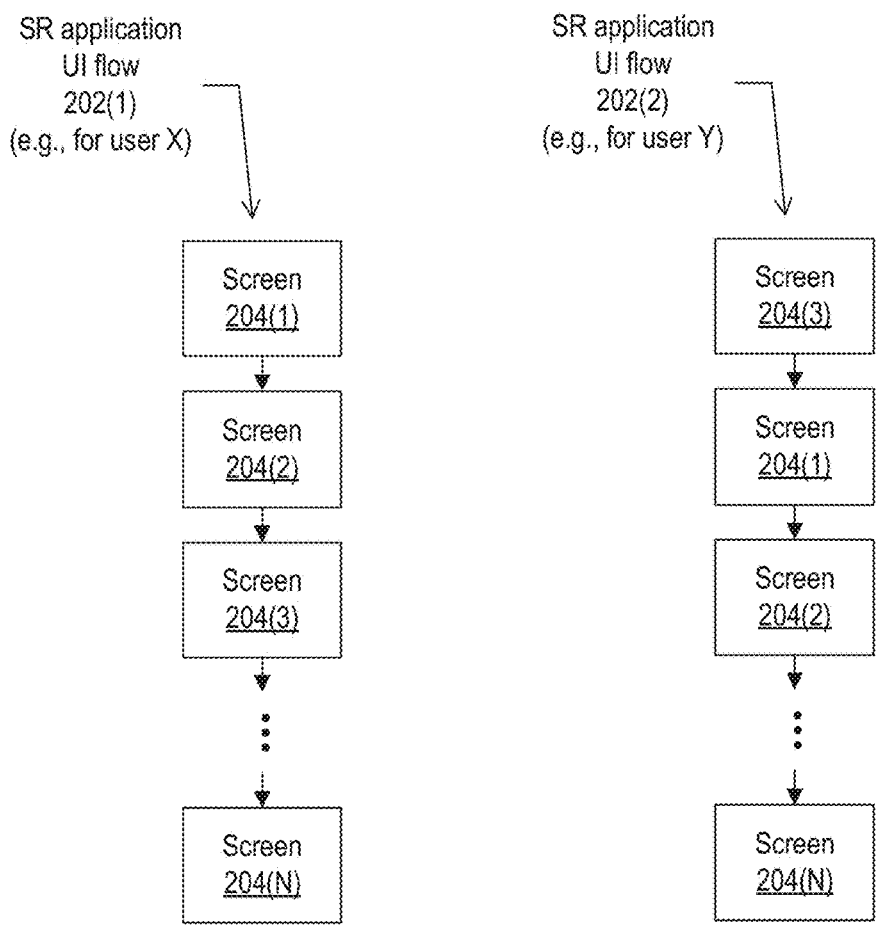
FIG. 2 depicts an example schematic of two different flows that may be determined for an application based on the presence of different users in an area, according to implementations of the present disclosure.

FIG. 2 depicts an example schematic of two different flows that may be determined for an application based on the presence of different users in an area, according to implementations of the present disclosure. Such different flows 202 may be presented in the SR application based on detecting different users X and Y, for example. Alternatively, the different flows may be presented based on detecting a same user X in different circumstances, such as in different areas of service or in different situations (e.g., at a catastrophic event response effort versus at a car dealership). In the first example, the flow 202(1) includes the presentation of a screen 204(1), followed by a screen 204(2), followed by a screen 204(3), up to a final screen 204(N). In the second example, the flow 202(2) includes the same screens presented in a different order. Different flows may also include sets of screens that differ in the screens that are being presented. For example, a first flow may present screens 204(1), 204(2), and 204(3) in some order, whereas a second flow may present screens 204(1), 204(2), and 204(4) in some order. Flows may also differ with respect to the timing of the displayed screens. For example, a first flow may present an initial screen 204(1) for 10 minutes, whereas a second flow may present the screen 204(1) for 5 minutes.

Figure 3:
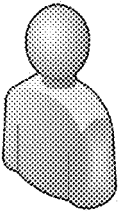
FIG. 3 depicts an example user interface, according to implementations of the present disclosure.

FIG. 3 depicts an example UI 302, such as the UI of the SR application 132, according to implementations of the present disclosure. In this example, the UI 302 presents at least a portion of the user data 118, such as the user's name, image, user ID number, a list of products used, the user's current location (inside a particular area of service). The UI 302 may also present the user's current state 126, determined based on biometric data as described above. The UI 302 may also present one or more dynamically determined screens 204 as part of a dynamically determined UI flow. In this example, the UI 302 is presenting a screen 204 to facilitate the processing of a homeowner's insurance claim. The form has been pre-populated with elements of the user data 118.

Figure 4:
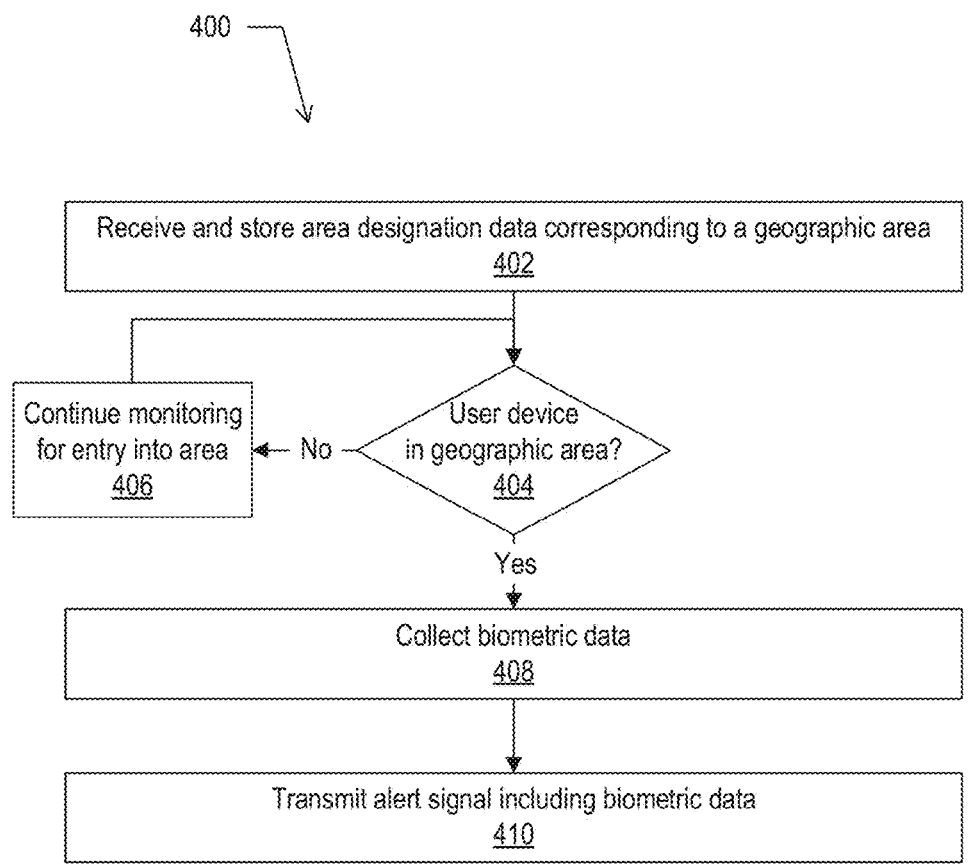
FIG. 4 depicts a flow diagram of an example process for transmitting an alert signal based on the presence of a computing device in an area, according to implementations of the present disclosure.

FIG. 4 depicts a flow diagram of an example process for transmitting an alert signal based on the presence of a computing device in an area, according to implementations of the present disclosure. Operations of the process may be performed by one or more of the user application 106, the server module(s) 116, the SR application 132, and/or other software module(s) executing on the user device 104, the server device(s) 114, the SR device 130, or elsewhere.

The area designation data 108 may be received by, and/or stored on, the user device 104 (402). Alternatively, the data 108 may be stored externally to the user device 104, in a location that is accessible by the user device 104 over one or more networks.

A determination is made (404) whether the user device 104 is currently in the geographic area of service, as described by the area designation data 108. In some examples, the user application 106 may periodically check (e.g., every five seconds) whether the user device 104 has entered the area. If not, the user application 106 may continue monitoring (406) for entry into the area. If it is determined that the user device 104 is in the area, an alert signal may be transmitted (410) to indicate that the user device 104 has entered the area. The alert signal may be sent to the server device(s) 114 or to the SR device 130 respectively, as described above. In some implementations, the alert signal may be sent after the user device 104 enters the area and remains in the area for a predetermined period of time. For example, the alert signal may be sent if the user device 104 is in the area for at least a minute.

In some implementations, the process may include collecting or retrieving biometric data regarding the user 102 (408). The alert signal may include biometric data, as described above.

Figure 5:
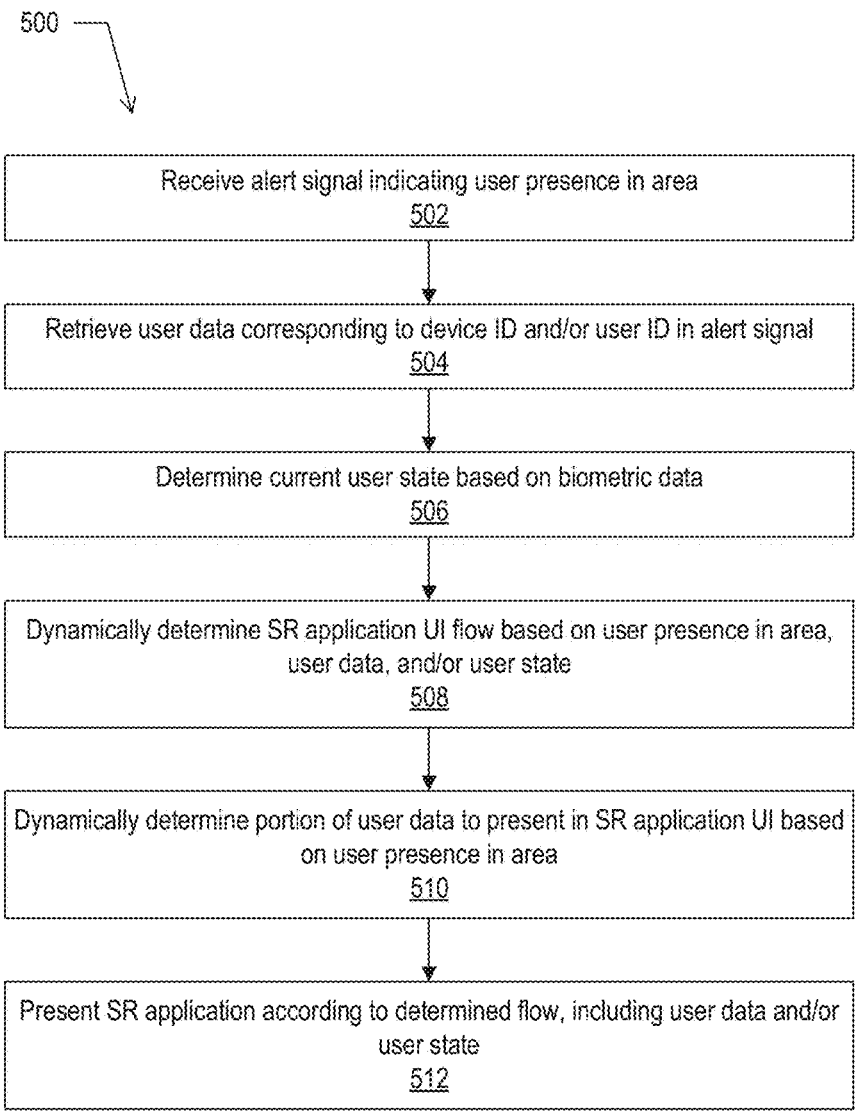
FIG. 5 depicts a flow diagram of an example process for determining an interface flow for an application, in response to receiving the alert signal, according to implementations of the present disclosure.

FIG. 5 depicts a flow diagram of an example process for determining an interface flow for an application, in response to receiving the alert signal, according to implementations of the present disclosure. Operations of the process may be performed by one or more of the user application 106, the server module(s) 116, the SR application 132, and/or other software module(s) executing on the user device 104, the server device(s) 114, the SR device 130, or elsewhere.

An alert signal may be received (502), indicating the presence of the user 102 and/or the user device 104 of the user 102 in the area of service. The user data 118 corresponding to the user 102 may be retrieved (504), based on the device ID and/or user ID included in the signal as described above. In some implementations, the current user state of the user 102 may be determined based on biometric data, as described above.

Based on the detected presence of the user 102 in the area, the user data of the user 102, and/or the current user state of the user 102, the UI flow of the SR application may be dynamically determined (508) as described above. In some implementations, a determination may also be (e.g., dynamically) made (510) to identify the portion of the user data to present in the UI of the SR application. The SR application may be presented (512) on the SR device in a state according to the dynamically determined UI flow and/or user data to be presented. In some instances, this may include launching the SR application. Alternatively, the SR application may already be executing when the dynamic determinations are made. In such instances, the current state of the SR application may be altered to reflect the determined UI flow and/or user data for presentation.

Figure 6:
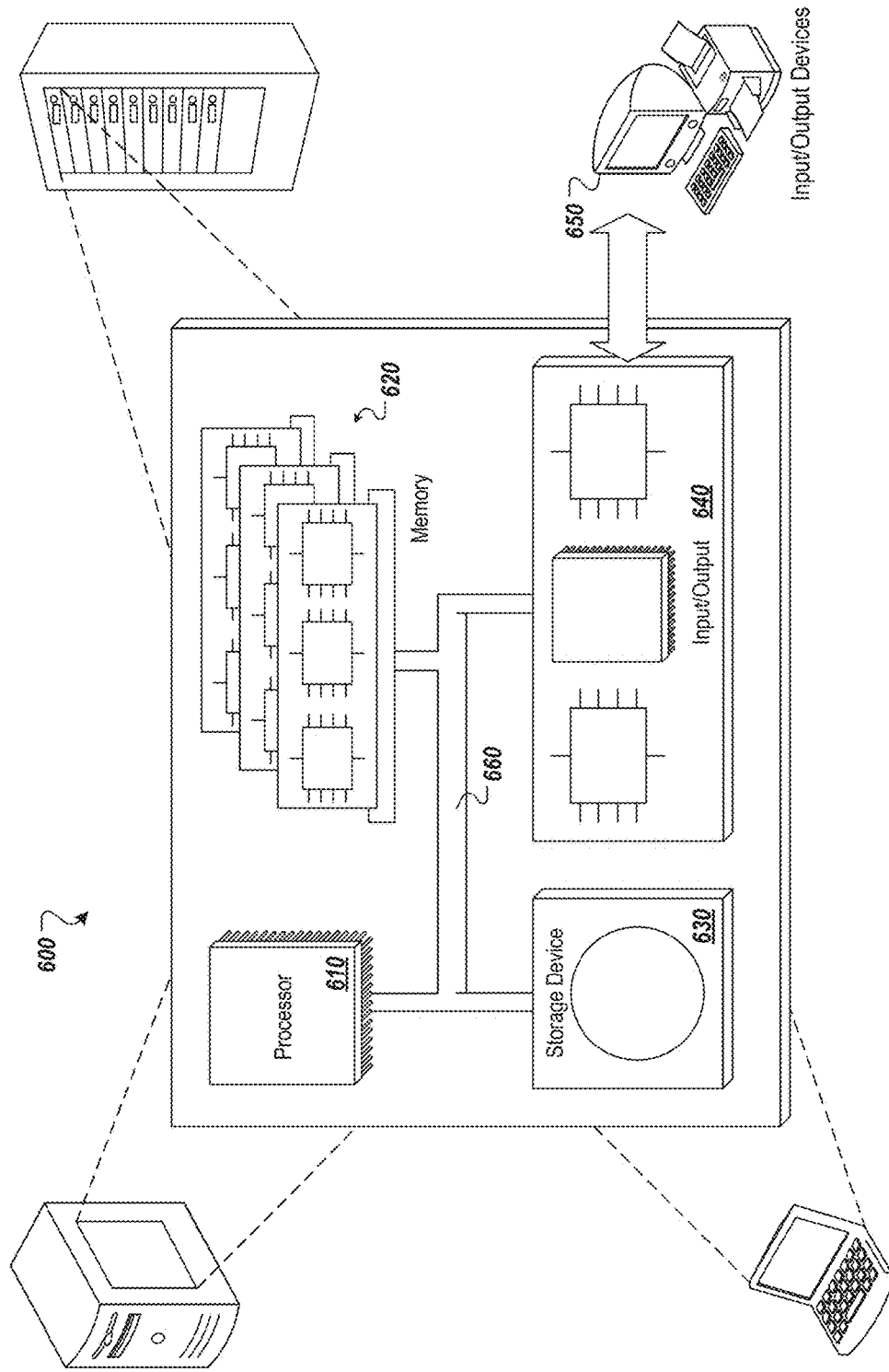
FIG. 6 depicts an example computing system, according to implementations of the present disclosure.

FIG. 6 depicts an example computing system, according to implementations of the present disclosure. The system 600 may be used for any of the operations described with respect to the various implementations discussed herein. For example, the system 600 may be included, at least in part, in one or more of the user device 104, the SR device 130, the server device(s) 114, and/or other computing device(s) or system(s) described herein. The system 600 may include one or more processors 610, a memory 620, one or more storage devices 630, and one or more input/output (I/O) devices 650 controllable through one or more I/O interfaces 640. The various components 610, 620, 630, 640, or 650 may be interconnected through at least one system bus 660, which may enable the transfer of data between the various modules and components of the system 600.

The processor(s) 610 may be configured to process instructions for execution within the system 600. The processor(s) 610 may include single-threaded processor(s), multi-threaded processor(s), or both. The processor(s) 610 may be configured to process instructions stored in the memory 620 or on the storage device(s) 630. The processor(s) 610 may include hardware-based processor(s) each including one or more cores. The processor(s) 610 may include general purpose processor(s), special purpose processor(s), or both.

The memory 620 may store information within the system 600. In some implementations, the memory 620 includes one or more computer-readable media. The memory 620 may include any number of volatile memory units, any number of non-volatile memory units, or both volatile and non-volatile memory units. The memory 620 may include read-only memory, random access memory, or both. In some examples, the memory 620 may be employed as active or physical memory by one or more executing software modules.

The storage device(s) 630 may be configured to provide (e.g., persistent) mass storage for the system 600. In some implementations, the storage device(s) 630 may include one or more computer-readable media. For example, the storage device(s) 630 may include a floppy disk device, a hard disk device, an optical disk device, or a tape device. The storage device(s) 630 may include read-only memory, random access memory, or both. The storage device(s) 630 may include one or more of an internal hard drive, an external hard drive, or a removable drive.

One or both of the memory 620 or the storage device(s) 630 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 600. In some implementations, the CRSM may include a data store that provides storage of computer-readable instructions or other information in a non-transitory format. The CRSM may be incorporated into the system 600 or may be external with respect to the system 600. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 610 and the memory 620 may be supplemented by, or incorporated into, one or more application-specific integrated circuits (ASICs).

The system 600 may include one or more I/O devices 650. The I/O device(s) 650 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 650 may also include one or more output devices such as a display, LED(s), an audio output device (e.g., a speaker), a printer, a haptic output device, and so forth. The I/O device(s) 650 may be physically incorporated in one or more computing devices of the system 600, or may be external with respect to one or more computing devices of the system 600.

The system 600 may include one or more I/O interfaces 640 to enable components or modules of the system 600 to control, interface with, or otherwise communicate with the I/O device(s) 650. The I/O interface(s) 640 may enable information to be transferred in or out of the system 600, or between components of the system 600, through serial communication, parallel communication, or other types of communication. For example, the I/O interface(s) 640 may comply with a version of the RS-232 standard for serial ports, or with a version of the IEEE 1284 standard for parallel ports. As another example, the I/O interface(s) 640 may be configured to provide a connection over Universal Serial Bus (USB) or Ethernet. In some examples, the I/O interface(s) 640 may be configured to provide a serial connection that is compliant with a version of the IEEE 1394 standard.

The I/O interface(s) 640 may also include one or more network interfaces that enable communications between computing devices in the system 600, or between the system 600 and other network-connected computing systems. The network interface(s) may include one or more network interface controllers (NICs) or other types of transceiver devices configured to send and receive communications over one or more networks using any network protocol.

Computing devices of the system 600 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 600 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical UI or a web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method performed by a first computing device, the method comprising:

providing, by the first computing device, area designation data that is transmitted to a second computing device that is a portable computing device;
receiving, by the first computing device, a first alert signal that is transmitted from the portable computing device to include an indication that the portable computing device is within a geographic area corresponding to the area designation data and location data for the portable computing device, as determined on the portable computing device based on the area designation data; and
responsive to receiving the first alert signal:
accessing by the first computing device, user data associated with a user of the portable computing device, the user data determined based at least partly on an identifier (ID) communicated by the first alert signal, and
sending a second alert signal from the first computing device to a third computing device to instruct an application executing on the third computing device to dynamically determine a user interface (UI) flow of the application based at least partly on the user data and a presence of the portable computing device in the geographic area, wherein the UI flow comprises an order of a plurality of screens displayed via the third computer device.

2. The method of claim 1, wherein:
the ID is a device ID that identifies the portable computing device; and
the user data is determined based on an association of the device ID with the user in a data structure accessible from the first computing device.

3. The method of claim 1, wherein the ID is a user ID that identifies the user.

4. The method of claim 1,
wherein the third computing device is configured to launch the application with the dynamically determined UI flow in response to receiving the second alert signal and based at least partly on the user data.

5. The method of claim 1, wherein:
the area designation data indicates the geographic area with reference to one or more geographic coordinates; and
the determination that the portable computing device is within the geographic area is based on a comparison of the area designation data to a current location of the portable computing device.

6. The method of claim 5, wherein the area designation data indicates the geographic area as one or more polygons each demarcated based on a respective set of geographic coordinates.

7. The method of claim 1, wherein:
the area designation data indicates the geographic area with reference to at least one beacon signal; and
the determination that the portable computing device is within the geographic area is based on detecting the at least one beacon signal at the portable computing device.

8. The method of claim 1, wherein at least a portion of the user data is presented within the application.

9. The method of claim 1, further comprising:
determining a state of the user of the portable computing device based at least partly on biometric data describing at least one physiological characteristic of the user; and
indicating the state of the user in the application.

10. The method of claim 9, wherein the UI flow of the application is further determined based on the state of the user.

11. A system, comprising:
a first computing device comprising at least one processor and a memory communicatively coupled to the at least one processor, the memory storing instructions which, when executed by the at least one processor, cause the at least one processor to perform operations comprising:
providing, by the first computing device, area designation data that is transmitted to a second computing device that is a portable computing device;
receiving, by the first computing device, a first alert signal that is transmitted from the portable computing device to indicate that the portable computing device is within a geographic area corresponding to the area designation data, as determined on the portable computing device based on the area designation data and location data for the portable computing device; and
responsive to receiving the first alert signal:
accessing, by the first computing device, user data associated with a user of the portable computing device, the user data determined based at least partly on an identifier (ID) communicated by the alert signal, and
sending a second alert signal from the first computing device to a third computing device to instruct an application executing on the third computing device to dynamically determine a user interface (UI) flow of the application based at least partly on the user data and a presence of the portable computing device in the geographic area, wherein the UI flow comprises an order of a plurality of screens displayed via the third computer device.

12. The system of claim 11, wherein:
the ID is a device ID that identifies the portable computing device; and
the user data is determined based on an association of the device ID with the user in a data structure.

13. The system of claim 11, wherein the ID is a user ID that identifies the user.

14. The system of claim 11,
wherein the third computing device is configured to cause the application to display the dynamically determined UI flow via a display of the third computing device in response to receiving the alert signal and based at least partly on the user data.

15. The system of claim 11, wherein:
the area designation data indicates the geographic area with reference to one or more geographic coordinates; and
the determination that the portable computing device is within the geographic area is based on a comparison of the area designation data to a current location of the portable computing device.

16. The system of claim 15, wherein the area designation data indicates the geographic area as one or more polygons each demarcated based on a respective set of geographic coordinates.

17. The system of claim 11, wherein:
the area designation data indicates the geographic area with reference to at least one beacon signal; and the determination that the portable computing device is within the geographic area is based on detecting the at least one beacon signal at the portable computing device.

18. The system of claim 11, the operations further comprising:
   determining a state of the user of the portable computing device based at least partly on biometric data describing at least one physiological characteristic of the user; and
   indicating the state of the user in the application.

19. The method of claim 18, wherein the UI flow of the application is further determined based on the state of the user.

20. One or more non-transitory computer-readable media storing instructions which, when executed by a first computing device, cause the first computing device to perform operations comprising:
   providing, by the first computing device, area designation data that is transmitted to a second computing device that is a portable computing device;
   receiving, by the first computing device, a first alert signal that is transmitted from the portable computing device to indicate that the portable computing device is within a geographic area corresponding to the area designation data, as determined on the portable computing device based on the area designation data and location data for the portable computing device; and
   responsive to receiving the first alert signal:
      accessing, by the first computing device, user data associated with a user of the portable computing device, the user data determined based at least partly on an identifier (ID) communicated by the alert signal, and
      sending a second alert signal from the first computing device to a third computing device to instruct an application executing on the third computing device to dynamically determine a user interface (UI) flow of the application based at least partly on the user data and a presence of the portable computing device in the geographic area, wherein the UI flow comprises an order of a plurality of screens displayed via the third computer device.

* * * * *

UNITED STATES PATENT AND TRADEMARK OFFICE
CERTIFICATE OF CORRECTION

| | |
|---|---|
| PATENT NO. | : 10,318,001 B1 |
| APPLICATION NO. | : 15/497750 |
| DATED | : June 11, 2019 |
| INVENTOR(S) | : James Malcolm Spears et al. |

Page 1 of 1

It is certified that error appears in the above-identified patent and that said Letters Patent is hereby corrected as shown below:

In the Specification

In Column 3, Lines 61-62, delete "to the to the" and insert -- to the --

In Column 5, Line 62, delete "user' s presence" and insert -- user's presence --

In Column 6, Line 41, delete "current in" and insert -- currently in --

In Column 6, Line 50, delete "in in range" and insert -- in range --

In the Claims

In Column 17, Line 11, in Claim 19, delete "The method of" and insert -- The system of --

Signed and Sealed this
Tenth Day of September, 2019

Andrei Iancu
*Director of the United States Patent and Trademark Office*